United States Patent [19]

Gesson et al.

[11] Patent Number: 4,789,665
[45] Date of Patent: Dec. 6, 1988

[54] ANTHRACYCLINES AND DRUGS CONTAINING THEM

[75] Inventors: Jean-Pierre Gesson, Chasseneuil du Poitou; Martine Mondon, Poitiers; Jean-Claude Jacquesy, Bruxerolles, all of France; Hans P. Kraemer, Marburg, Fed. Rep. of Germany

[73] Assignees: Laboratoires Hoechst S. A., Puteaux, France; Behringwerke Aktiengesellschaft, Marburg, Fed. Rep. of Germany

[21] Appl. No.: 941,604

[22] Filed: Dec. 15, 1986

[30] Foreign Application Priority Data

Dec. 17, 1985 [FR] France .................... 85-18661

[51] Int. Cl.⁴ .................... A61K 31/70; C07H 15/24
[52] U.S. Cl. .................... 514/34; 536/6.4
[58] Field of Search .................... 536/6.4; 514/34

[56] References Cited

U.S. PATENT DOCUMENTS 4,591,637 5/1986 Acton et al. .................... 536/6.4

Primary Examiner—Johnnie R. Brown
Assistant Examiner—Elli Peselev
Attorney, Agent, or Firm—Finnegan, Henderson, Farabow, Garrett & Dunner

[57] ABSTRACT

The present invention relates to new anthracyclines corresponding to the general formula I below:

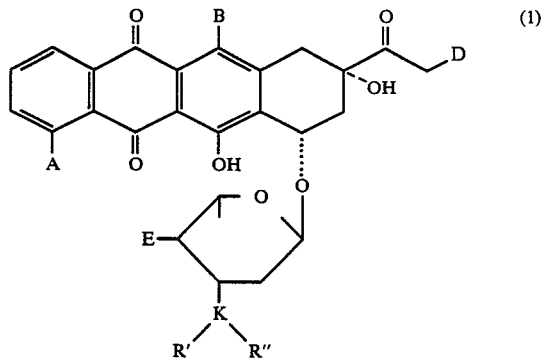

in which R' and R'', which may be identical or different, denote a hydrogen atom (and in this case R' is different from R'') or the group —(CH$_2$)$_n$—R$_1$—(CH$_2$)$_m$—R$_2$ where n is between 1 and 6,
  m is between 0 and 4 (with the proviso, of course, that if m=0, R$_2$ is nonexistent)
R$_1$ denotes one of the following groups:

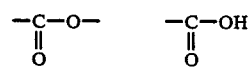

(in this case, m=0)

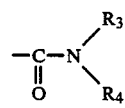

(in this case m=0) where R$_3$ and R$_4$, which may be identical or different, denote a hydrogen atom or a substituted or unsubstituted alkyl group)
—C≡N (in this case m=0)
—S—
—O—(with the proviso that m is other than 0)

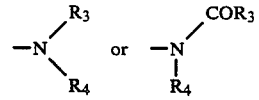

(m=0 and R$_3$ R$_4$ have the same meaning as above) and R$_2$ denotes (in the case where m is other than 0) a hydrogen atom or alkyl or alkoxy groups or

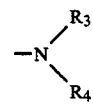

(R$_3$ and R$_4$ having the same meaning as above).

These compounds possess cytotoxic properties for treating L1210 leukemia.

13 Claims, No Drawings

ANTHRACYCLINES AND DRUGS CONTAINING THEM

The present invention relates to new anthracyclines and to drugs containing them.

A great deal of effort, continuously expended during recent years by different research teams, has enabled the anthracycline family to be enlarged, these compounds nowadays constituting one of the most promising classes of drugs in respect of its anticancer activity.

Continuing the study which has already been proceeding for several years (see, in particular, French Pat. Nos. 83/05,217, 85/13,877, 84/03,634, 84/09,405 and 85/10,063), the Applicant has developed new anthracycline derivatives in which the pharmacological properties of this family are advantageously modified.

The subject of thepresent invention is new anthracyclines represented by the formula I below:

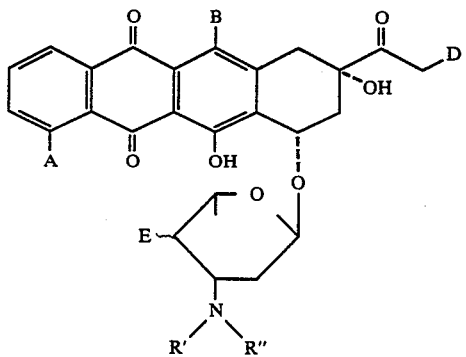

in which:
A denotes OCH$_3$ or OH or H groups,
B denotes an OH group or a hydrogen atom,
D denotes a hydrogen atom or an OH group,
E denotes an OH group or a hydrogen atom,
and R' and R'', which may be identical or different, denote a hydrogen atom (and in this case R' is different from R'') or the group —(CH$_2$)$_n$—R$_1$—(CH$_2$)$_m$—R$_2$ where
n is between 1 and 6,
m is between 0 and 4 (with the proviso, of course, that if m=0, R$_2$ is nonexistent)
R$_1$ denotes one of the following groups:

(in this case, m=0)

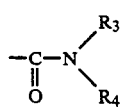

(in this case m=0 where R$_3$ and R$_4$, which may be identical or a different, denote a hydrogen atom or substituted or unsubstituted alkyl group)
—C≡N (in this case m=0)
—S—
—O— (with the proviso that m is other than 0)

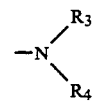

(m=0 and R$_3$ and R$_4$ have the same meaning as above)

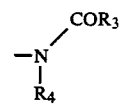

(m=0 and R$_3$ and R$_4$ have the same meaning as above)
and
R$_2$ denotes (in the case where m is other than 0) a hydrogen atom or alkyl or alkoxy groups or

(R$_3$ and R$_4$ having the same meaning as above)

Some of these new derivatives have exceptional cytotoxic properties, as described later in the cell proliferation test. The Applicant has been able to achieve these results by means of the "functionalization" of the alkyl radicals R' and R''.

Among the different derivatives according to the present invention which are endowed with very advantageous pharmacological effects, it is appropriate to mention the following in particular:
3'-N-(cyanomethyl)daunorubicin
3'-N,N-bis(cyanomethyl)daunorubicin
3'-N-(2-methoxyethyl)daunorubicin
3'-N-cyanomethyl-3'-N-(2-methoxyethyl)daunorubicin
3'-N-[(N,N-diethylcarbamoyl)methyl]daunorubicin
3'-N,N-bis[(N,N-diethylcarbamoyl)methyl]daunorubicin
3'-N-(carbomethoxymethyl)daunorubicin
3'-N-[2-(2-methoxyethoxy)ethyl]daunorubicin
3'-N,N-bis[2-(2-methoxyethoxy)ethyl]daunorubicin The invention also provide a process for the preparation of the above anthracycline derivatives and in particular of 4'-epi and 4'-deoxy derivatives of the doxorubicin family, of the daunorubicin family and of the carminomycin family, wherein doxorubicin or daunorubicin or carminomycin, or one of their corresponding salts, is reacted in a suitable solvent, such as DMF, and in the presence of a teritary amine with one or more halogenated derivatives chosen from the group which comprises, in particular, halonitrile, halo-N,N-diethylacetamide, methylhaloacetate, 1-halo-2-(2-methoxyethoxy)ethane and 1-halo-2-methoxyethane, and wherein the desired product is isolated in a suitable manner.

The invention will be better understood with the aid of the additional description which follows, which relates to examples of implementing the processes or of preparations of the derivatives according to the present invention, and also to an account of pharmacological experiments.

It must nevertheless be clearly understood that these examples of implementation and this account of pharmacological experiments are given exclusively by way of illustration of the subject of the invention, and in no way constitute a limitation thereof.

EXAMPLES

PREPARATION OF 3'-N-(CYANOMETHYL)- AND 3'-N,N-BIS(CYANOMETHYL)DAUNORUBICIN

Iodoacetonitrile (10 eq.) is added to a mixture of daunorubicin hydrochloride (100 mg; 0.18 mmol) and Et$_3$N (0.54 mmol) in 15 ml of DMF. After 48 h at room temperature, 3'-N,N-bis(cyanomethyl)daunorubicin (7 mg, 6.3%), 3'-N-(cyanomethyl)daunorubicin (58 mg, 57%) and unreacted daunorubicin (16 mg, 16.6%) are separated in order of increasing polarity.

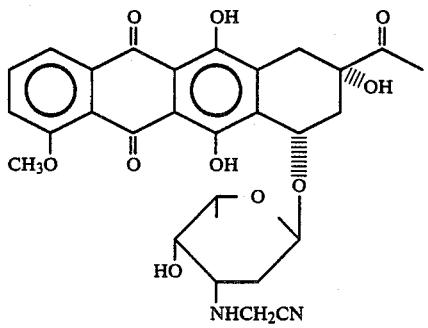

3'-N-(CYANOMETHYL)DAUNORUBICIN

Yld.=57%

Melting point: 134°–140° C. (dec.)

MS: (FAB-): 566

NMR (CDCl$_3$) 200 MHz: 1.35 (doublet, J=5 Hz, 3H); 2.42 (singlet, 3H); 3.00 (ABq, 2H); 3.59 (singlet, 1H); 3.69 (singlet, 1H); 4.07 (singlet, 3H); 5.25 (sharp signal, 1H); 5.50 (sharp signal, 1H); 7.38 (doublet, J=7.5 Hz, 1H); 7.77 (triplet, J=7.5 Hz, 1H); 8.00 (doublet, J=7.5 Hz, 1H); 13.23 (singlet, 1H); 13.95 (singlet, 1H).

IR (CH$_2$Cl$_2$): 3600, 3500, 1710, 1610, 1550, 1440 cm$^{-1}$.

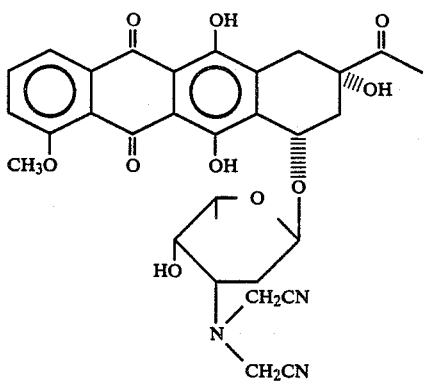

3'-N,N-BIS(CYANOMETHYL)DAUNORUBICIN

Yld.=6.3%

Melting point: 155°–165° C.

NMR (CDCl$_3$) 200 MHz: 1.34 (doublet, J=5.5 Hz, 3H); 2.40 (singlet, 3H); 3.10 (ABq, 2H); 3.80 (singlet); 4.08 (singlet, 3H); 4.29 (broad singlet, 1H); 5.26 (sharp signal, 1H); 5.57 (sharp signal, 1H); 7.38 (doublet, J=7.5 Hz, 1H); 7.79 (triplet, J=7.5 Hz, 1H); 8.03 (doublet, J=7.5 Hz, 1H); 13.28 (singlet, 1H); 14.02 (singlet, 1H).

IR (CH$_2$Cl$_2$): 3700, 3500 (broad), 2980, 2920, 2840, 1710, 1610, 1580, 1420, 1380, 1350 cm$^{-1}$.

PREPARATION OF 3'-N-(2-METHOXYETHYL)DAUNORUBICIN

2-Iodoethyl methyl ether (15 eq.) is added to a mixture of daunorubicin hydrochloride (30 mg; 0.054 mmol) and Et$_3$N (0.16 mmol) in 1.5 ml of DMF. After 48 h at room temperature, 3'-N-(2-methoxyethyl)daunorubicin (60%) is separated from the residual daunorubicin (22%).

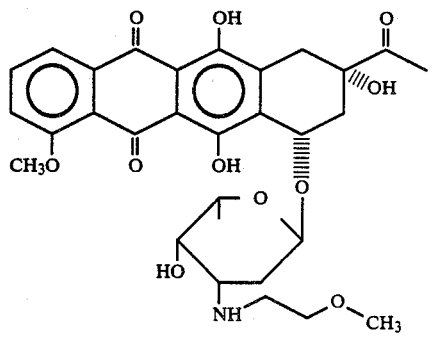

3'-N-(2-METHOXYETHYL)DAUNORUBICIN

Yld.: 60%

Melting point: (Kofler stage): 113° C. (dec.)

MS: (FAB-): 585 (12%); 515 (13%), 409 (9%), 380 (11%), 321 (12%), 301 (100%)

[α]$_D$=253° (C=0.15; CHCl$_3$)

NMR (CDCl$_3$) 200 MHz: 1.38 (doublet, J=5.5 Hz, 3H); 2.41 (singlet, 3H); 2.74 (triplet, J=5 Hz, 2H); 3.32 (singlet, 3H); 3.46 (triplet, J=5 Hz, 2H); 4.09 (singlet, 3H); 4.73 (broad singlet, 1H); 5.31 (sharp signal, 1H); 5.53 (sharp signal, 1H); 7.40 (doublet, J=7.5 Hz, 1H); 7.80 (triplet, J=7.5 Hz, 1H); 8.06 (doublet, J=7.5 Hz, 1H).

PREPARATION OF 3'-N-CYANOMETHYL-3'-N-(2-METHOXYETHYL)DAUNORUBICIN

Iodoacetonitrile (15 eq.) is added to a mixture of 3'-N-(2-methoxyethyl)daunorubicin (10 mg; 0.017 mmol), obtained above, and Et$_3$N (0.05 mmol) in DMF (0.5 ml). After 48 h at room temperature, 3'-N-cyanomethyl-3'-N-(2-methoxyethyl)daunorubicin (10.2 mg; 98%) is obtained.

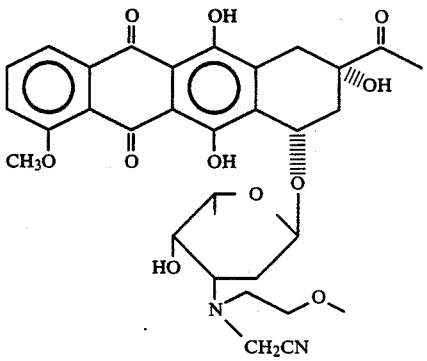

3'-N-CYANOMETHYL-3'-N-(2-METHOXYETHYL)DAUNORUBICIN

Yld.=98%

[α]$_D$=378° (C=0.07; CHCl$_3$)

NMR (CDCl$_3$) 200 MHz: 1.38 (doublet, J=5.5 Hz, 3H); 2.43 (singlet, 3H); 3.10 (ABq, 2H); 3.35 (singlet, 3H); 3.66 (singlet); 4.10 (singlet, 3H); 4.57 (singlet, 1H); 5.31 (sharp signal, 1H); 5.59 (sharp signal, 1H); 7.40 (doublet, J=7.5 Hz, 1H); 7.79 (triplet, J=7.5 Hz, 1H); 8.05 (doublet, J=7.5 Hz, 1H); 13.32 (singlet, 1H); 14.02 (singlet, 1H).

Melting point (Kofler stage): 120° (dec.)

The following were obtained in the same manner:

(a)

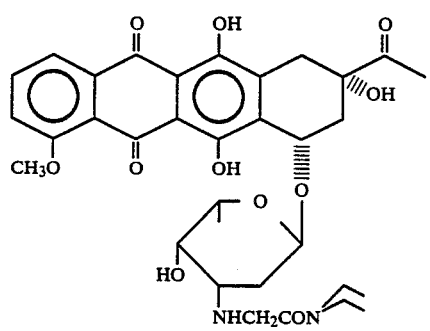

3'-N-[(N,N-DIETHYLCARBAMOYL)METHYL]-DAUNORUBICIN

NMR: 1.37 (doublet, J=5.5 Hz, 3H); 2.41 (singlet, 3H); 4.08 (singlet, 3H); 4.77 (broad singlet, 1H); 5.31 (sharp signal, 1H); 5.53 (sharp signal, 1H); 7.39 (doublet, J=7.5 Hz, 1H); 7.78 (triplet, J=7.5 Hz, 1H); 8.03 (doublet, J=7.5 Hz, 1H); 13.30 (singlet, 1H); 13.66 (singlet, 1H).

(b)

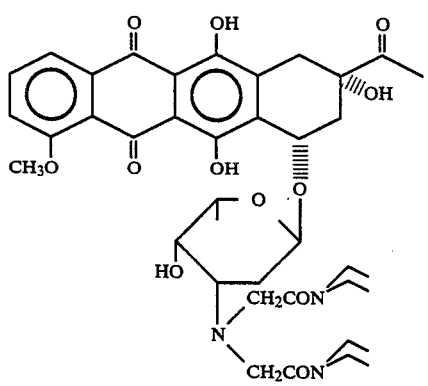

3'-N,N-BIS[(N,N-DIETHYLCARBAMOYL)METHYL]DAUNORUBICIN

NMR: 2.40 (singlet, 3H); 4.09 (singlet, 3H); 5.30 (sharp signal, 1H); 5.57 (sharp signal, 1H); 7.38 (doublet, J=7.5 Hz, 1H); 7.77 (triplet, J=7.5 Hz, 1H); 8.05 (doublet, J=7.5 Hz, 1H); 13.31 (singlet, 1H); 13.65 (singlet, 1H).

(c)

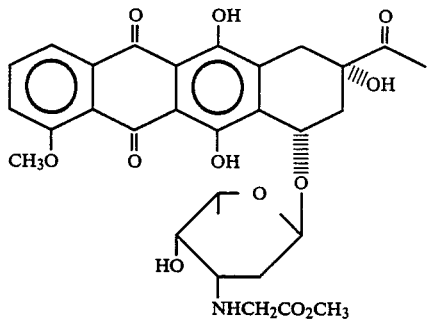

3'-N-(CARBOMETHOXYMETHYL)DAUNORUBICIN

Melting point: 142°-148° C.

NMR (CDCl$_3$) 200 MHz: 1.36 (doublet, J=5.5 Hz, 3H); 2.41 (singlet, 3H); 3.10 (ABq, 2H); 3.41 (singlet, 2H); 3.52 (singlet, 1H); 3.70 (singlet, 3H); 4.09 (singlet, 3H); 5.29 (sharp signal, 1H); 5.52 (sharp signal, 1H); 7.40 (doublet, J=7.5 Hz, 1H); 7.79 (triplet, J=7.5 Hz, 1H); 8.06 (doublet, J=7.5 Hz, 1H).

(d)

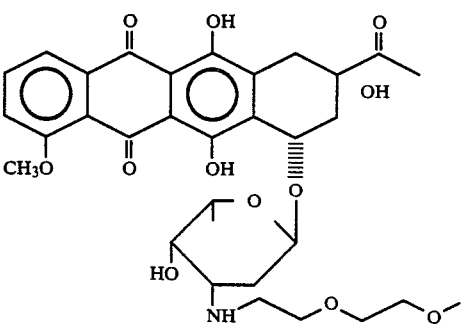

3'-N-[2-(2-METHOXYETHOXY)ETHYL]-DAUNORUBICIN

Yld.=44%

Melting point: 70°-75° C.

[α]$_D$=270° (C=0.1; CHCl$_3$)

NMR (CDCl$_3$) 200 MHz: 1.36 (doublet, J=5.5 Hz, 3H); 2.41 (singlet, 3H); 3.02 (ABq, 2H); 3.33 (singlet, 3H); 4.07 (singlet, 3H); 4.69 (broad singlet, 1H); 5.25 (sharp signal, 1H); 5.50 (sharp signal, 1H); 7.38 (doublet, J=5 Hz, 1H); 7.76 (triplet, J=7.5 Hz, 1H); 8.00 (doublet, J=7.5 Hz, 1H).

(e)

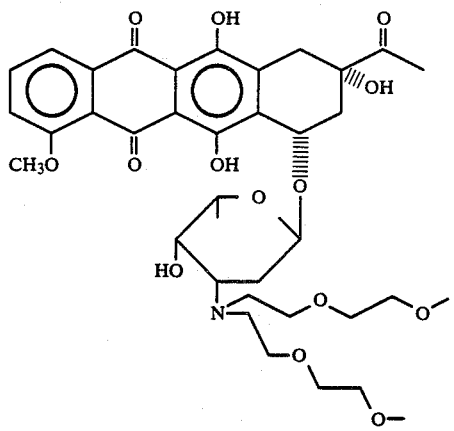

3'-N,N-BIS[2-(2-METHOXYETHOXY)ETHYL]-DAUNORUBICIN

Yld.=9%

$[\alpha]_D = 294°$ (C=0.07; CHCl$_3$)

NMR (CDCl$_3$) 200 MHz: 1.34 (doublet, J=5 Hz, 3H); 2.42 (singlet, 3H); 3.12 (ABq, 2H); 3.31 (singlet, 6H); 4.09 (singlet, 3H); 4.74 (broad singlet, 1H); 5.30 (sharp signal, 1H); 5.58 (sharp signal, 1H); 7.40 (doublet, J=7.5 Hz, 1H); 7.79 (triplet, J=7.5 Hz, 1H); 8.02 (doublet, J=7.5 Hz, 1H); 13.31 (singlet, 1H); 14.0 (singlet, 1H).

The cytotoxic properties of some derivatives claimed according to the invention are demonstrated in the cell proliferation tests which are summarized in Table I below.

The experimental protocol was performed according to the procedure of HAMBURGER and SALMON on leukemia L 1210 strain cells. Some modifications were introduced in the procedure of HAMBURGER and SALMON, and in particular:

the conditioned medium was replaced by McCoy5A. The number of cells in a dish was reduced to 5×10$^2$ cells per dish on account of the high covering efficiency of leukemia L 1210.

Cells were incubated with various concentrations of the test substance for 1 hour at 37° C. The cells were then washed twice with McCoy5A, and finally applied in an agar upper layer according to the method of HAMBURGER and SALMON.

In addition, parallel experiments were carried out with continuous incubation and with various concentrations of the test substance by mixing the latter with the upper layer before application.

The dishes were kept in an incubator with 5% CO$_2$, 20% O$_2$, at 95% relative humidity for 5 to 7 days at 37° C. After this period, the colonies having a diameter greater than 60 μm were counted with an inverted microscope.

The results were expressed as a percentage of the number of colonies formed from treated L 1210 relative to an untreated control. The coefficient of variation of repeated experiments was less than 15%.

The results are presented in Table I.

TABLE I

| PRODUCT | IC$_{50}$ in μg/ml (continuous exposure) |
|---|---|
| 3'-N—(cyanomethyl)-daunorubicin | 0.0028 |
| 3'-N,N—bis(cyanomethyl)-daunorubicin | 0.08 |
| 3'-N—(2-methoxyethyl)-daunorubicin | 0.01 |
| 3'-N—cyanomethyl-3'-N—(2-methoxyethyl)daunorubicin | 0.09 |
| 3'-N—[(N,N—diethylcarbamoyl)-methyl]daunorubicin | 0.28 |
| 3'-N,N—bis[(N,N—diethylcarbamoyl)-methyl]daunorubicin | 0.65 |
| 3'-N—(carbomethoxymethyl)daunorubicin | 0.24 |
| 3'-N—[2-(2-methoxyethoxy)ethyl]-daunorubicin | 0.07 |
| 3'-N,N—bis[2-(2-methoxyethoxy)-ethyl]daunorubicin | 0.22 |
| DOXORUBICIN (reference) | 0.02 |
| DAUNORUBICIN (reference) | 0.02 |

The drugs containing the derivatives according to the present invention are generally administered at doses of between 0.001 and 25 mg/kg/day.

The derivatives according to the general formula I are preferably administered orally but, according to requirements they can be administered by the other routes: parenterally, subcutaneously, intravenously, intramuscularly, intraperitoneally or transcutaneously.

This administration can also be carried out in combination with excipients or diluents which are pharmaceutically acceptable.

We claim:

1. A anthracycline represented by the formula 1 below:

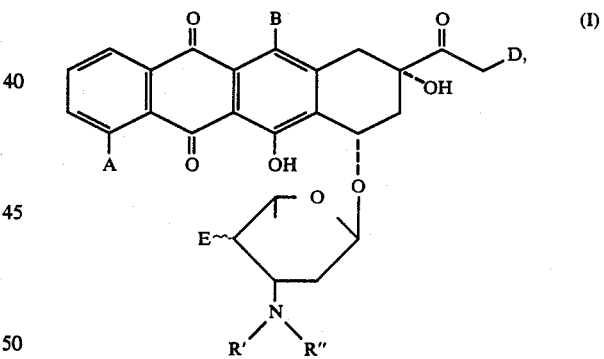

in which:

A denotes OCH$_3$ or OH or H groups,

B denotes an OH group or a hydrogen atom,

D denotes a hydrogen atom or an OH group,

E denotes an OH group or a hydrogen atom, and R' and R", which may be identical or different, denote a hydrogen atom, and in this case R' is different from R", or the group —(CH$_2$)$_n$—R$_1$—(CH$_2$)$_m$—R$_2$ where n is between 1 and 6, m is between 0 and 4, that if m=0, R$_2$ is nonexistent, R$_1$ denotes one of the following groups:

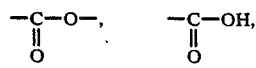

in this case, m=0

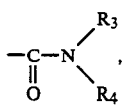

in this case m=0 where $R_3$ and $R_4$, which may be identical or different, denote a hydrogen atom or an alkyl group,

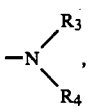

m=0 and $R_3$ and $R_4$ have the same meaning as above,

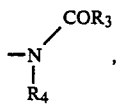

m=0 and $R_3$ and $R_4$ have the same meaning as above, and $R_2$ denotes, in the case where m is other than 0, a hydrogen atom or lower alkyl or lower alkoxy groups or

where $R_3$ and $R_4$ having the same meaning as above.

2. An anthracycline as claimed in claim 1, wherein D denotes an OH group.
3. An anthracycline as claimed in claim 1, wherein D denotes a hydrogen atom.
4. An anthracycline as claimed in claim 1, wherein A denotes an OH group and D denotes a hydrogen atom.
5. An anthracycline as claimed in claim 1, which is a 4'-epi derivative.
6. An anthracycline as claimed in claim 1, which is a 4'-deoxy derivative.
7. An anthracycline as claimed in claim 1, which is 3'-N-(2-methoxyethyl)daunorubicin.
8. An anthracycline as claimed in claim 1, which is 3'-N-[(N,N-diethylcarbamoyl)methyl]daunorubicin.
9. An anthracycline as claimed in claim 1, which is 3'-N,N-bis[(N,N-diethylcarbamoyl)methyl]daunorubicin.
10. An anthracycline as claimed in claim 1, which is 3'-N-(carbomethoxymethyl)daunorubicin.
11. An anthracycline as claimed in claim 1, which is 3'-N-[2-(2-methoxyethoxy)ethyl]duanorubicin.
12. An anthracycline as claimed in claim 1, which is 3'-N,N-bis[2-(2-methoxyethoxy)ethyl]daunorubicin.
13. A pharmaceutical composition comprising an effective amount of a compound of formula (I) of claim 1 and a pharmaceutically acceptable carrier.

* * * * *